United States Patent [19]

Sarstedt et al.

[11] 4,206,077

[45] Jun. 3, 1980

[54] AGENT FOR FACILITATING THE COUNTING OF THROMBOCYTES IN BLOOD SAMPLES

[76] Inventors: Walter Sarstedt, 5223 Nümbrecht, Rommelsdorf; Djuro Rodjak, Konrad-Adenauer-Str. 17, 7208 Spaichingen, both of Fed. Rep. of Germany

[21] Appl. No.: 937,875

[22] Filed: Aug. 29, 1978

[30] Foreign Application Priority Data

Oct. 7, 1977 [DE] Fed. Rep. of Germany ....... 2745151

[51] Int. Cl.² .................. G01N 33/16; C09K 3/00
[52] U.S. Cl. .................. 252/408; 23/230 B; 424/3; 424/101; 424/146
[58] Field of Search .......... 252/408; 23/230 B, 230 R; 195/103.5 R; 424/101, 3, 146

[56] References Cited

U.S. PATENT DOCUMENTS

| | | | |
|---|---|---|---|
| 764,913 | 7/1904 | Chapman | 424/176 |
| 1,530,280 | 3/1925 | Molz | 424/146 |
| 3,574,137 | 4/1971 | De Casperis | 252/408 |
| 3,607,783 | 9/1971 | Tata et al. | 252/408 |
| 3,632,735 | 1/1972 | Kita | 252/408 |
| 3,634,581 | 1/1972 | Thomas | 252/408 |
| 3,640,896 | 2/1972 | De Casperis | 252/408 |
| 3,873,467 | 3/1975 | Hunt | 252/408 |
| 3,884,579 | 5/1975 | Mauthner | 252/408 |
| 4,007,008 | 2/1977 | Becker et al. | 252/408 |

OTHER PUBLICATIONS

Rehm, M. M., et al., Plant Physiology, vol. 51, No. 5, pp. 946–948 (1973).
Lessler, M. A., et al., Proc. Society for Experimental Biology and Medicine, vol. 142, No. 2, pp. 548–553 (1973).
C.A., vol. 79, p. 135, 28276z (1973).
C.A., vol. 78, p. 104, 80510q (1973).
C.A., vol. 73, p. 138, 1623z (1970).
C.A., vol. 60, 11235h (1964).
The Merck Index, Eighth Edition, Merck & Co., Inc., Rahway, N.J., p. 659, "Mercuric Chloride", (1968).

*Primary Examiner*—Teddy S. Gron
*Attorney, Agent, or Firm*—Browdy and Neimark

[57] ABSTRACT

An agent for facilitating the counting of thrombocytes in blood samples in the presence of erythrocytes, comprises an aqueous solution of mercuric chloride in a concentration of between 1.2 and 4.0 g/l. The pH of this solution is adjusted to 1.5 to 4.8, preferably by the addition of hydrochloric acid or nitric acid or mercuric nitrate. 2 mls of this solution is mixed with 20 $\mu$l of the blood to be tested. The erythrocytes are decolored in this solution and the thrombocytes become more brilliant in the microscopic image so that they are relatively easy to count.

11 Claims, No Drawings

AGENT FOR FACILITATING THE COUNTING OF THROMBOCYTES IN BLOOD SAMPLES

This invention relates to an agent for facilitating the counting of thrombocytes in blood samples in the presence of erythrocytes.

When directly counting thrombocytes in blood samples by means of a microscope, the erythrocytes at the same time present interfere particularly seriously because they are strongly red colored and in part cover the thrombocytes. The counting of thrombocytes according to this direct method has therefore up to now always been subject to a rather wide unreliability or has not been possible.

An object of this invention is to improve the counting of thrombocytes in presence of interfering erythrocytes.

According to the present invention, an agent is proposed which consists of an aqueous solution of mercuric chloride in a concentration of between 1.2 and 4.0 g/l, the pH of which is adjusted to 1.5 to 4.8, 2 mls of this solution being mixed with 20 $\mu$l of the blood to be examined. The agent causes a decoloring of the erythrocytes, while the thrombocytes become more brilliant in the microscopic image, so that they are relatively easy to count.

The mixing ratio of the amount of solution and of the amount of blood is at an optimum for a blood generally of a normal thrombocyte content, since by the dilution achieved in this way a reliable counting with a minimum error rate is possible. In special cases, this mixing ratio may be different, however, as will be set forth hereinafter.

Preferably it is proposed that the concentration of the solution of mercuric chloride is between 1.5 and 3.5 g/l. In this range, the brilliancy of the thrombocytes is particularly satisfactory, and thereby the counting is particularly easy.

The optimum value within the foregoing mentioned ranges is at a pH of 2.5 and at a concentration of mercuric chloride of 2.75 g/l.

These values are also at an optimum for another reason:

In the case of a pathologically reduced thrombocyte content, the counting in the microscope becomes unreliable with the mixing ratio indicated, because there are only a very few thrombocytes in the image, a higher blood concentration of 50 $\mu$l or possibly even 100 $\mu$l may be used for the indicated amount of 2 ml of the solution. Then, the number of thrombocytes in the microscopic image field rises, and the counting will become more reliable. At the same time, however, as a result of the higher pH of the blood (in excess of 7.0) also the pH of the mixture will be shifted to a greater extent upwardly (in direction of the neutral point), than was the case for the small blood quantity of 20 $\mu$l. The pH of 2.5 given as an optimum, is so low, however, that even when adding 100 $\mu$l blood to 2 mls of the solution the pH of the mixture does not exceed 4.5. Generally, the pH of the mixture even stays below 4.0.

In the event a larger blood quantity is to be added to the initially proposed solution in its wide concentration range, it is very generally proposed that the pH of the solution be adjusted so low that the pH of the mixture after the addition of blood stays below 4.5, preferably below 4.0.

The pH is preferably adjusted by the addition of hydrochloric acid or nitric acid or also mercuric nitrate.

EXAMPLE 2.75 g mercuric chloride were added to 1000 ml distilled water and agitated into solution. Then, the pH was adjusted by the addition of hydrochloric acid. 20 $\mu$l blood were added to 2.0 mls of the foregoing mentioned solution and carefully mixed, until the erythrocytes decolored (haemolysis). From this mixture, the thrombocytes were counted by means of a count chamber method, microscopically.

The examinations are carried at at room temperature. An affect of the temperature on the effectiveness of the agent has not been observed. In this test, vein blood was used which had been rendered non-coagulatable by means of di-K-EDTA.

We claim:

1. A method for facilitating the counting of thrombocytes in blood samples in the presence of erythrocytes, comprising:
   combining a blood sample containing erythrocytes with an aqueous solution of 1.2–4.0 g/l mercuric chloride, the pH of which has been adjusted to 1.5–4.8, in a quantity sufficient to cause a decoloring of the erythrocytes while permitting the thrombocytes to become more brilliant in a microscopic image.

2. A method in accordance with claim 1 wherein the pH adjustment is accomplished by the addition of hydrochloric acid, nitric acid, or mercuric nitrate.

3. A method in accordance with claim 1 wherein the pH has been adjusted to 2.0–4.5.

4. A method in accordance with claim 1 wherein the solution comprises 1.5–3.5 g/l of mercuric chloride.

5. A method in accordance with claim 1 wherein the solution comprises 2.75 g/l mercuric chloride and the pH has been adjusted to 2.5.

6. A method in accordance with claim 1 wherein the ratio of solution to blood sample is about 1000:1–5.

7. A method in accordance with claim 1 wherein the pH of the solution is adjusted to a value within said range such that the pH of the combined blood sample-solution does not exceed 4.5.

8. A method in accordance with claim 7 wherein the pH is adjusted to a value within said range such that the pH of the combined blood sample-solution does not exceed 4.0.

9. A treated blood sample in which the counting of thrombocytes in the presence of erythrocytes is facilitated, comprising:
   a sample of blood containing erythrocytes combined with an aqueous solution of 1.2–4.0 g/l mercuric chloride, the pH of which has been adjusted to 1.5–4.8, in a quantity sufficient to cause a decoloring of the erythrocytes while permitting the thrombocytes to become more brilliant in a microscopic image.

10. A treated blood sample in accordance with claim 9 wherein the pH has been adjusted by means of hydrochloric acid, nitric acid or mecuric nitrate.

11. An agent for use in the method of claim 1, consisting essentially of an aqueous solution of 1.2–4.0 g/l mercuric chloride and a sufficient quantity of hydrochloric acid, nitric acid or mercuric nitrate to adjust the pH to 1.5–4.8.